United States Patent [19]

Kablaoui

[11] 4,058,540

[45] Nov. 15, 1977

[54] PREPARATION OF 2-ALKANOYLOXYALKANOIC ACIDS

[75] Inventor: Mahmoud S. Kablaoui, Wappingers Falls, N.Y.

[73] Assignee: Texaco Inc., New York, N.Y.

[21] Appl. No.: 733,633

[22] Filed: Oct. 18, 1976

[51] Int. Cl.$^2$ .................. C09F 5/00; C11C 3/00
[52] U.S. Cl. .................. 260/405; 260/410; 260/413; 260/535 R; 560/266
[58] Field of Search ......... 260/410, 410.9 D, 410.9 E, 260/488 F, 491, 405, 535 R, 413

[56] References Cited

U.S. PATENT DOCUMENTS

| | | | |
|---|---|---|---|
| 2,346,272 | 4/1944 | Pecherer | 260/488 F |
| 3,796,735 | 3/1974 | Duranlean et al. | 260/488 F |

*Primary Examiner*—Winston A. Douglas
*Assistant Examiner*—John F. Niebling
*Attorney, Agent, or Firm*—Thomas H. Whaley; Carl G. Ries; George J. Darsa

[57] ABSTRACT

2-Alkanoyloxyalkanoic acids are prepared by contacting a nitroalkylnitrate and/or a nitroalcohol with an alkanoic acid in the presence of calcium oxide or a calcium carboxylate.

11 Claims, No Drawings

PREPARATION OF 2-ALKANOYLOXYALKANOIC ACIDS

BACKGROUND OF THE INVENTION

This invention relates to a method for preparing 2-alkanoyloxyalkanoic acids. In particular, this invention relates to a method of preparing 2-alkanoyloxyalkanoic acids from nitroalkylnitrates and nitroalcohols.

The preparation of 2-alkanoyloxyalkanoic acids can be undertaken by the steps of chlorinating, hydrolyzing and esterifying an alkanoic acid. Such a procedure for preparing 2-alkanoyloxyalkanoic acids is not particularly attractive inasmuch as it involves several steps resulting in many instances in low selectivities or yields of desired product. A method has now been found whereby individual or mixtures of 2-alkanoyloxyalkanoic acids can be produced in good yields directly from nitronitrates or nitroalcohols.

It is therefore an object of this invention to provide a novel method for preparing 2-alkanoyloxyalkanoic acids.

Another object of this invention is to provide a method for preparing 2-alkanoyloxyalkanoic acids from nitronitrates or nitroalcohols.

Yet another object of this invention is to provide a method for preparing 2-alkanoyloxyalkanoic acids in good yields.

Other objects and advantages will become apparent from a reading of the following detailed description and examples.

SUMMARY OF THE INVENTION

Broadly, this invention contemplates a method of preparing a 2-alkanoyloxyalkanoic acid which comprises contacting a nitroalkylnitrate or a nitroalcohol with an alkanoic acid in the presence of calcium oxide or a calcium carboxylate.

According to this invention, the contemplated 2-alkanoyloxyalkanoic acids are prepared from nitroalkylnitrates or nitroalcohols or mixtures thereof corresponding to the formula:

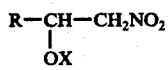

where X is $NO_2$ or hydrogen and where R is an alkyl Group of from 1 to 50 carbon atoms, preferably 2 to 20 carbons.

More particularly, the nitroalkylnitrates employable in the instant process correspond to the formula:

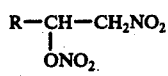

where R is as described above. Illustrative of the nitroalkylnitrates I mention 1-nitro-2-butylnitrate, 1-nitro-2-pentylnitrate, 1-nitro-2-hexylnitrate, 1-nitro-2-octylnitrate, 1-nitro-2-decylnitrate, 1-nitro-2-dodecylnitrate, 1-nitro-2-teteradecylnitrate and 1-nitro-2-hexadecylnitrate. The nitronitrates employable in the instant method typically can be formed by nitrooxidizing a 1-olefin at low temperatures followed by reduction with, for example, nitric oxide as described in U.S. Pat. No. 3,282,983.

Alternately, the nitroalcohols contemplated in the instant method correspond to the formula:

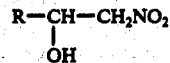

where R is as described above. Typical nitroalcohols employable as reactants in the instant method include 1-nitro-2-butanol, 1-nitro-2-pentanol, 1-nitro-2-hexanol, 1-nitro-2-heptanol, 1-nitro-2-octanol, 1-nitro-2-undecanol, 1-nitro-2-tridecanol, 1-nitro-2tetradecanol and 1-nitro-2-hexadecanol. Mixtures of nitroalkylnitrates and nitroalcohols can also be employed as initial reactants and the mixture converted to 2-alkanoyloxyalkanoic acids according to this invention.

In particular, the present method comprises contacting the nitroalkylnitrate or nitroalcohol or mixtures thereof with an alkanoic acid in the presence of calcium oxide or a calcium carboxylate. Calcium carboxylates contemplated in the instant method include calcium salts of $C_2$-$C_{10}$ alcanoic acids such as, for example, calcium acetate, calcium propionate, calcium butanoate and calcium heptanoate. Preferably calcium oxide or calcium acetate is employed.

The alkanoic acid utilized in the instant method and reacted with the nitronitrate or nitroalcohol is one having 2 to 20 carbon atoms. Illustrative of the alkanoic acids employed I mention acetic acid, propionic acid, butanoic acid, isobutanoic acid, pentanoic acid, hexanoic acid, octanoic acid, decanoic acid, undecanoic acid, dodecanoic acid, hexadecanoic acid, heptadecanoic acid, octadecanoic acid, and eicosanoic acid. In general, the acids utilized in the present method correspond to the formula:

where $R^1$ is an alkyl group of 1 to 19 carbons.

More specifically, the instant method is further explained by the following equation:

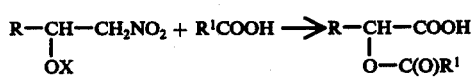

where X, R and $R^1$ are as heretofore defined. In the practice of the method outlined above, it is essential that the reaction be conducted in the presence of calcium oxide or a calcium carboxylate as more fully explained below. Nitronitrates or nitroalcohols have not been found to react with an alkanoic acid to form 2-alkanoyloxyalkanoic acids in the absence of the calcium compound.

The method described herein is conducted at temperatures above about 100° C. and up to about 200° C., preferably from about 118° C. to 140° C. thereby forming the 2-alkanoyloxyalkanoic acid. It has been found that at temperatures from about 60° C. and up to about 100° C. no measurable amounts of 2-alkanoyloxyalkanoic acid is formed. Instead the nitronitrate or nitroalcohol and alkanoic acid reactants in the presence of the calcium compound form a mixture of nitroolefin and nitrocarboxylate. Undertaking the reaction at temperatures above 100° C. in accordance with the instant method, nitroolefin and nitrocarboxylate are initially formed as intermediate products and are in turn converted to the 2-alkanoyloxyalkanoic acid. While not wishing to be bound by any theory underlying the reaction where a plurality of intermediate products are formed ultimately leading to the 2-alkanoyloxyalkanoic acid, it has been observed that in the course of the reaction the ratio of the nitroolefin to nitrocarboxylate intermediates is approximately 1:1 indicating an apparent equilibrium between the intermediate nitrocompounds under the reaction conditions set forth herein. The equilibrium has been found to continue albeit that the amount of intermediates in the reaction diminish in the course of 2-alkanoyloxyalkanoic acid formation. To form significant and measurable amounts of 2-alkanoyloxyalkanoic acid product the reaction is conducted under the reaction conditions described herein for periods ranging of from about one-half to 24 hours. For example, after approximately 4 hours at 118° C. substantial amounts of 2-alkanoyloxyalkanoic acids are formed and after approximately 6 hours the principle product recoverable from the reaction is the desired 2-alkanoyloxyalkanoic acid. Continuing the reaction for longer periods of time substantially diminishes the presence of intermediate products such that the product comprises 95 percent or higher 2-alkanoyloxyalkanoic acid and the intermediates comprise from 5 percent or less. A by-product of the reaction is hydroxylamine ($NH_2OH$).

In accordance with the method described herein the contacting of the reactants can be undertaken employing mole ratios of nitroalkylnitrate or nitroalcohol or mixtures thereof to alkanoic acid of between about 1:1 and 1:10. Mole ratios of nitroalkylnitrate or nitroalcohol or mixtures thereof to calcium oxide or calcium carboxylate of from about 1:1 to 1:3 are utilized. A significant aspect of the ratio of reactants is that the moles of alkanoic acid be at least equivalent and preferably in excess to the moles of nitrocompound reactant. The higher ratios of alkanoic acid are also preferred in that the acid functions not only as a reactant but additionally as the reaction medium. The contacting of the reactants is desirably carried out under conditions of agitation. If desired, an inert liquid diluent can also be present and may be desirable in those instances where the nitronitrate or nitroalcohol is viscous or solid at the reaction temperature. Suitable diluents, that is, those inert to the reaction, are those having a boiling point of at least 100° C. and up to about 250° C. including, for example, a wide range of $C_8$ to $C_{18}$ alkanes illustrated by octane, nonane, decane, dodecane, pentadecane and octadecane and alkyl benzenes such as toluene, xylene, ethylbenzene, isopropylbenzene, cyclohexylbenzene and phenylbenzene. The diluent, when employed, can be provided in amounts of from about 5 to 98 weight percent based on the weight of the charged nitrocompound. At the completion of the 2-alkanoyloxyalkanoic acid formation reaction, the acid product can be converted, if desired, to a 2-hydroxyalkanoic acid by contacting the product with water at temperatures of about 80° to 100° C.

Illustrative of the 2-alkanoyloxyalkanoic acids prepared according to the inventive method include 2-acetoxypropionic acid, 2-acetoxybutanoic acid, 2-propoxypentanoic acid, 2-butoxyhexanoic acid, 2-butoxyoctanoic acid, 2-acetoxydecanoic acid, 2-propoxydodecanoic acid, 2-acetoxytetradecanoic acid, 2-butoxyhexadecanoic acid, 2-acetoxypropionic acid, 2-acetoxy-2-methylpropionic acid 2-octatoxydecanoic acid, 2-dodecanoxyhexadecanoic acid and 2-octadecanoxytetradecanoic acid.

At the completion of the reaction the 2-alkanoyloxyalkanoic acid can be recovered, for example, by springing the acid from the reaction mixture at about room temperature employing a dilute aqueous solution of a non-oxidizing mineral acid, such as hydrochloric acid, sulfuric acid, or phosphoric acid. The acid of choice is hydrochloric acid. The 2-alkanoyloxyalkanoic acid is thereafter extracted employing a non-polar aprotic solvent, such as diethylether, carbon tetrachloride, chloroform or benzene. The aqueous layer contains hydroxylamine, unreacted lower molecular weight alkanoic acids when employed as initial reactants and calcium salt. The solvent layer after separation contains the 2-alkanoyloxyalkanoic acid along with minor amounts of nitroolefin and nitrocarboxylate. In those instances where a higher molecular weight alkanoic acid was initially employed, the solvent layer may also contain the same. Higher purities of 2-alkanoyloxyalkanoic acid can be recovered by distillation thereby removing solvent, intermediate products and higher molecular weight alkanoic acids.

The 2-alkanoyloxyalkanoic acids prepared according to the instant method are useful as intermediates in the preparation of plasticizers by reactions with alkanols, for the preparation of alkenoic acids, such as acrylic acid and methacrylic acid, by pyrolysis of the alkoxy group or by hydrolysis and dehydration of the alkoxy group. Alkenoic acids are useful monomers for the preparation of such polymers as polyacrylates and polymethacrylates and alkenoic acids are additionally useful in such applications as pesticides, photographic compounds and weed killers. The 2-hydroxyalkanoic acids are likewise useful in preparing alkenoic acids and polymerization to polymers.

In order to more fully illustrate the nature of this invention and the manner of practicing the same the following examples are presented.

EXAMPLE 1

To 12.4 grams (0.05 mole) of 1-nitro-2-decylnitrate and 2.8 grams (0.05 mole) of calcium oxide maintained at 10° C. there was introduced 100 milliliters of acetic acid. After maintaining at 118° C. for 6 hours, the reaction mixture was cooled to 15° C. and the contents added to 200 milliliters of water and 25 milliliters of aqueous HCl (50 percent). The solution was extracted with four 75 milliliter portions of diethylether and the solution stripped of ether by rotatory evaporation to give 10.7 grams (approximately 90 percent yield) of product identified by infrared and nuclear magnetic resonance analyses as 2-acetoxydecanoic acid containing less than five percent nitrodecene and 2-acetoxy-1-nitrodecane.

EXAMPLE 2

To 10.0 grams (0.05 mole) of 1-nitro-2-decanol and 2.8 grams (0.05 mole) of calcium oxide maintained at 10° C. there was introduced 100 milliliters of acetic acid. After maintaining at 118° C. for 2 hours, the reaction mixture, upon analysis, was determined to contain 37 weight percent 2-acetoxydecanoic acid, 32 weight percent 1-nitrodecene, and 31 weight percent 2-acetoxy-1-nitrodecane. After maintaining the reaction at 118° C. for 8 hours and extracting as in Example 1, 10.5 grams of 2-acetoxydecanoic acid (approximately 90% yield) was recovered.

EXAMPLE 3

To 12.4 grams (0.05 mole) of 1-nitro-2-decylnitrate and 7.9 grams (0.05 mole) of calcium acetate maintained at 10° C. there was introduced 100 milliliters of acetic acid. The reactants were heated to 118° C. for 6 hours, extracted as in Example 1, and 10.7 grams (approximately 90% yield) of product was recovered and identified as 2-acetoxydecanoic acid.

EXAMPLE 4

To 10.0 grams (0.05 mole) of 1-nitro-2-decanol and 7.9 grams (0.05 mole) of calcium acetate maintained at 10° C. was added 100 millilliters of acetic acid. Heating for 6 hours at 118° C. and extracting as in Example 1 above, provided 10.7 grams (approximately 90% yield) of 2-acetoxydecanoic acid.

EXAMPLE 5

To 12.4 grams (0.05 mole) of 1-nitro-2-decylnitrate there was added 100 milliliters of acetic acid and the mixture was heated to 118° C. for 6 hours. The reaction mixture was subsequently cooled to 15° C., 200 milliliters of water added and the solution extracted with four 100 milliliter portions of diethylether. The solution was stripped of ether and the product was identified as containing 95 percent of the starting materials indicating that essentially no reaction occured.

EXAMPLE 6

To 24.8 grams (0.10 mole) of 1-nitro-2-decylnitrate and 5.6 grams (0.10 mole ) of calcium oxide maintained at 10° C. there was added 300 milliliters of acetic acid and the reaction mixture slowly heated to 118° C. Samples of the mixture were taken at 60° C., 100° C. and at 118° C. and after 2, 4 and 6 hours at 118° C. Analysis of the extracted products by gas chromatograph, infrared and nuclear magnetic resonance are reported as weight percent in the Table below.

TABLE

| Temp. °C. | Time, hrs | Nitrodecene | 2-acetoxy-1-nitrodecane | 2-acetoxy-decanoic acid |
|---|---|---|---|---|
| 60 | — | 30 | — | — |
| 100 | — | 50 | 50 | — |
| 118 | — | 42.5 | 42.5 | 15 |
| 118 | 2 | 33 | 33 | 35 |
| 118 | 4 | 20 | 20 | 60 |
| 118 | 6 | 2.5 | 2.5 | 95 |

I claim:

1. A method of preparing a 2-alkanoyloxyalkanoic acid which comprises contacting a nitroalkylnitrate or a nitroalcohol or mixtures thereof corresponding to the formula:

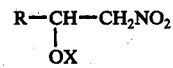

where X is $NO_2$ or hydrogen and where R is an alkyl group of from 1 to 50 carbon atoms with an alkanoic acid having from 2 to 20 carbon atoms in the presence of calcium oxide or a calcium carboxylate at a temperature of from above about 100° C. and up to about 200° C. employing mole ratios of nitroalkylnitrate or nitroalcohol to alkanoic acid of between 1:1 and 1:10.

2. A method according to claim 1 wherein said temperature is from about 118° C. to 140° C.

3. A method according to claim 1 wherein a mixture of nitroalkylnitrate and nitroalcohol is employed.

4. A method according to claim 1 wherein the mole ratio of nitroalkylnitrate or nitroalcohol to calcium oxide or calcium carboxylate is from about 1:1 to 1:3.

5. A method according to claim 1 wherein calcium oxide is employed.

6. A method according to claim 1 wherein said calcium carboxylate is calcium acetate.

7. A method according to claim 1 wherein said alkanoic acid is acetic acid.

8. A method according to claim 1 wherein said nitroalkylnitrate is 1-nitro-2-decylnitrate.

9. A method according to claim 1 wherein said nitroalcohol is 1-nitro-2-decanol.

10. A method according to claim 1 wherein said 2-alkanoyloxyalkanoic acid is 2-acetoxydecanoic acid.

11. A method according to claim 1 wherein said 2-alkanoyloxyolkanoic acid is thereafter contacted with water at from about 80° to 100° C. forming a 2-hydroxyalkanoic acid.

* * * * *